(12) United States Patent
Erpicum et al.

(10) Patent No.: US 6,368,623 B1
(45) Date of Patent: Apr. 9, 2002

(54) PULVERULENT CORN-STEEP

(75) Inventors: Thomas Erpicum, Liege (BE); Marie-Hélène Saniez, Saint Andre (FR)

(73) Assignee: Roquette Freres, Lestrem (FR)

( * ) Notice: Subject to any disclaimer, the term of this patent is extended or adjusted under 35 U.S.C. 154(b) by 0 days.

(21) Appl. No.: 09/542,119

(22) Filed: Apr. 4, 2000

(30) Foreign Application Priority Data

Apr. 8, 1999 (FR) .............................................. 99 04392

(51) Int. Cl.[7] .................................................. A61K 9/20
(52) U.S. Cl. ........................ 424/464; 424/400; 424/439; 424/489; 514/960; 435/41; 435/42
(58) Field of Search ................................ 424/400, 439, 424/441, 442, 464, 489; 514/960; 435/41, 42

(56) References Cited

U.S. PATENT DOCUMENTS

| | | | |
|---|---|---|---|
| 2,859,114 A | 11/1958 | Watson et al. | |
| 3,655,396 A | * 4/1972 | Goto et al. | 99/9 |
| 4,359,528 A | 11/1982 | Devos et al. | |
| 5,593,855 A | * 1/1997 | Lee et al. | 435/41 |
| 5,891,708 A | 4/1999 | Saniez et al. | |
| 5,902,615 A | 5/1999 | Saniez et al. | |

OTHER PUBLICATIONS

K.N. Wright, Corn Chemistry and Technology, 1987, pp447–478.
Chemical abstracts, vol. 84, No. 21, CS 159 853 A.
Chemical abstracts, vol. 130, No. 7, JP 338 584 A.
Patent abstracts of Japan, vol. 009, No. 205, JP 60 075 240 A.

* cited by examiner

*Primary Examiner*—Thurman K. Page
*Assistant Examiner*—Charesse L. Evans
(74) *Attorney, Agent, or Firm*—Henderson & Sturm LLP

(57) ABSTRACT

The invention relates to a pulverulent corn-steep without a drying substrate, said corn-steep containing lactic acid.

It also relates to a method of obtaining this pulverulent corn-steep as well as to its use in the fermentation industry.

3 Claims, No Drawings

PULVERULENT CORN-STEEP

FIELD OF THE INVENTION

The present invention relates to a pulverulent corn-steep without a drying substrate.

It also relates to a particular method of preparing said pulverulent corn-steep and to its uses in industry.

BACKGROUND OF THE INVENTION

Corn-steep, a term frequently used by the person skilled in the art, refers to the concentrated steep waters which result from the steeping of maize.

The steeping of maize in water is the first step in the extraction of starch in wet starch works. This steeping allows the swelling of the maize grains and the elimination of highly fermentable soluble matter contained in these grains. It consists in keeping the maize in silos for a given period of time within hot water containing a small quantity of sulphurous anhydride, this in order to facilitate the later separation of protein, cellulose and starch and, moreover, to stop the growth of undesirable micro-organisms.

Two essential phenomena take place simultaneously during steeping: the first consists in a diffusion of soluble matter from the maize grain towards the steep water whilst the second consists in a fermentation of this soluble matter in the steep water by lactic bacteria, the steeping conditions (presence of sulphites, reducing sugars, temperature) being favorable for the speedy development of this bacterial flora.

The main interest of these concentrated steep waters, usually called corn-steep by the skilled person, is their composition in essential nutrients, resulting from the transfer of the soluble matter of the grain. These nutrients constitute factors which favor the growth of micro-organisms as well as the production of secondary metabolites and make the corn-steep an ideal source of nutrient substances in the fermentation industries.

Indeed, corn-steep constitutes a source of choice of organic nitrogen through the distribution and the forms of its amino acids: free, peptide, protein, as well as a source of carbon (lactic acid) and phosphate (phytic acid) with a delayed effect. A significant content of vitamin and trace elements completes the interest of corn-steep as a nutrient source for the growth of micro-organisms and the induction of secondary metabolites when the corn-steep is associated with one or several sources of carbon (glucose, maltodextrin, starch, sucrose . . . ).

Moreover, it constitutes a nutrient source which is relatively cheap by comparison with yeast extracts which represent the reference material in this field and which are also used in human and animal feeding.

Furthermore, it is known that the use of corn-steep to replace complex nitrogen sources such as cotton or soya proteins, makes it possible to increase substantially antibiotic production yields.

However, corn-steep in liquid form presents problems of settling in the course of time, which is especially bothersome for transporting, storing and pumping the product. It must be stored in stirred and thermostatically controlled tanks to limit the development of its composition. This is all the more true when corn-steep is consumed in small quantities at a time by certain fermentation industries. In this case, it is particularly important to control its preservation. Obtaining corn-steep in dry form has then been considered.

Corn-steep has a water content of 45 to 55%. Evaporation to eliminate more than half of the water which it contains cannot be considered in view of the cost of evaporation on the one hand and the sensitivity to heat of certain nutrients on the other hand.

Drying through atomisation of liquid corn-steep has then been studied.

This technique, very widespread in the industry, has allowed the drying of products well known as difficult to dry, such as products which are sensitive to heat or highly hygroscopic. However, in the case of corn-steep, the person skilled in the art has met with gluing problems. Indeed, if the drying of certain products does not present any problems, i.e. the powder comes steadily out of the drying chamber or tower and has satisfactory appearance and flow properties, the liquid corn-steep, on the other hand, being rich in amino acids and hygroscopic substances, is subject to gluing.

This gluing manifests itself in deposits at various levels of the drying chamber and its ancillary equipment, deposits which generate losses and a deterioration of the product which can require stopping production with cleaning cycles which are costly in time, material and labour. Gluing can also happen downstream of drying when the powder, after a more or less lengthy storing period, loses its fluidity and forms lumps.

It is therefore very difficult to atomise corn-steep because of the particularly hygroscopic nature of the organic acids and the salts which it contains and especially the potassium lactate which is present in a large proportion (Corn Chemistry and Technology—K. N. WRIGHT 466–467).

To overcome these gluing problems, methods, sometimes empirical ones, have been applied at the industrial level, such as the addition to the product to be atomised of drying substrates, anti-agglomerating agents or dessicating powders.

In the food-processing industries, substrates frequently used are maltodextrins and glucose syrups. However, their incorporation rates are limited by the diluting effect which they exert on the product and by their high cost. Furthermore, such products cannot be subjected to a later heat treatment, such as sterilisation, as their high content of free sugars makes them subject to caramelization. Moreover, these compositions are highly hygroscopic which leads to lumping phenomena during storage.

It was then proposed in patent U.S. Pat. No. 2,859,114 that maize fibres be mixed with corn-steep so that it is absorbed by these fibres, thus making a drying operation possible. However, this method has the disadvantage of bringing to the corn-steep a high content of insoluble matter which is not desirable in the applications envisaged, especially fermentation.

Indeed, such a product very quickly shows settling phenomena during storage and through this a heterogeneous distribution of nutrient substances.

Furthermore, the product shows at the end an insufficient corn-steep concentration.

Other solutions, like the one described in the patent U.S. Pat. No. 3,655,396 consist in completely eliminating the lactic acid from the corn-steep. The lactic acid having indeed been blamed for the problems of drying corn-steep without it being clearly explained, it is eliminated with yeasts able to metabolise it, the culture medium obtained being afterwards dried on drums or through atomisation.

However, such a method has the drawback of depriving corn-steep of an important source of carbon on the one hand, but also of a precursor which is particularly interesting in the culture of diauxic micro-organisms.

There was therefore the need for a dry form of corn-steep with retained nutrient value and solubility.

SUMMARY OF THE INVENTION

Strengthened by this assessment, the inventors have therefore sought to perfect a pulverulent corn-steep, the qualities of which are retained and without the defects previously described for corn-steeps in powder form according to prior art.

And it is to the credit of the inventors that they have succeeded against all expectations, after carrying out in-depth research on the subject, in preparing a pulverulent corn-steep without being faced with gluing problems, this pulverulent corn-steep being without the defects noticed for the corn-steeps in powder form according to prior art, whilst retaining its initial qualities. The inventors have highlighted, in a surprising and unexpected manner, that such pulverulent corn-steep can be prepared without a drying substrate and without previous separation treatment, in special conditions starting from liquid corn-steep, with an atomisation process which had never made it possible in the past to obtain directly and without gluing corn-steep in powder form with the nutrient qualities intact, improved even, with satisfactory solubility and without any tendency to become lumpy.

It is all the more surprising that the atomisation of liquid corn-steep appeared, according to the patents U.S. Pat. No. 2,859,114 and U.S. Pat. No. 3,655,396, impossible without a drying substrate or without eliminating a fraction of the corn-steep.

MORE DETAILED DESCRIPTION

The invention relates, therefore, in the first place to a pulverulent corn-steep without a drying substrate. The term "drying substrate" designates the soluble or insoluble organic compounds likely to absorb liquid corn-steep or to modify its activity in water. These substrates known to the skilled person are in particular plant fibres, spent grain, brans, proteins, polysaccharides, carbohydrates, dessicants.

The essential feature of the pulverulent corn-steep according to the invention stems from the fact that it contains lactic acid. Lactic acid is understood as the D and L forms of lactic acid as well as its salts. Preferably, this lactic acid content is greater than or equal to 5% by weight dry or, even more preferably, equal to or greater than 10% by weight dry. Consequently it retains its qualities in relation to the pulverulent corn-steeps according to prior art from which the lactic acid would have been eliminated and does not have the drawbacks of insolubility or caramelization of the corn-steeps according to prior art dried on substrates of cellulose fibres or maltodextrins.

Advantageously, pulverulent corn-steep according to the invention has a metal ions content of between 1 and 5% by weight (dry/dry). Preferably this content is between 2 and 4% by weight (dry/dry).

The inventors have indeed demonstrated after long research that this second characteristic advantageously made it possible to obtain a pulverulent corn-steep which retained its initial properties and nutrient qualities.

Thus, beyond a 5% content in metal ions, corn steep becomes unusable in a fermentation medium as it brings an excess of metals unfavorable to the growth of micro-organisms.

Moreover, below a 1% content in metal ions, it is not possible to obtain a pulverulent corn-steep without the help of a drying substrate or without eliminating some of its constituent elements, such as lactic acid.

It is preferred that the metal ions are chosen from the group constituted of zinc, magnesium, calcium, strontium, barium or lithium salts, on their own or mixed with one another. In particular, magnesium salts are perfectly suitable. Indeed, these constitute an input in $mg^{2+}$ ions, the fundamental role of which in the growth and metabolism of numerous micro-organisms is known. This cation is indeed vital in the stabilisation of the cellular structure and involved in most of the metabolic mechanisms as an enzymatic cofactor.

Because of this, the nutrient qualities of pulverulent corn-steep according to the invention are not only preserved but also improved. It is understood then that these nutrient qualities combined with the ease of storing and implementation are an unquestionable advantage, for instance, in the preparation of culture media intended for fermentation.

The pulverulent corn-steep according to the invention has also other advantageous characteristics. One can mention its very good aptitude for being compressed and its very good aptitude for being mixed with other products.

The invention relates in the second place to a method of preparing a pulverulent corn-steep without a drying substrate and containing lactic acid.

The pulverulent corn-steep according to the invention is likely to be obtained by carrying out an enrichment of a liquid corn-steep with at least one metal salt before atomisation.

It has been noted, against all expectation, that such an enrichment step allowed the atomisation of the liquid corn-steep without generating gluing or lumpiness problems and without eliminating previously the lactic acid which it contains.

Indeed the inventors have demonstrated that the drying problems met in the methods of prior art were due to the fact that the potassium lactate present in great quantities in the corn-steep could not be crystallised. In enriching the corn steep with metal salt, the potassium lactate is displaced, through the salt effect, towards a form of lactate which can be crystallised. The corn-steep thus enriched is therefore easy to atomise, without it being necessary to add a drying substrate or to eliminate the lactic acid or other compound constituting the corn-steep.

The pulverulent corn-steep according to the invention is capable of being obtained according to a multitude of variants of the method but especially through a method comprising the following steps:

enrichment of the liquid corn-steep with at least one metal salt,
  atomisation of the enriched liquid corn steep,
  recovery of the pulverulent corn-steep thus obtained.

Concerning the enrichment of the liquid corn-steep, it is preferred that the metal salt is chosen from the group consisting of zinc, magnesium, calcium, strontium, barium and lithium salts. According to a preferred embodiment of the invention, magnesium oxide is chosen. As an indication, there is added to the liquid corn-steep a quantity of MgO of approximately 3% in dry weight expressed relative to the dry matter of the liquid corn-steep (dry/dry).

The liquid corn-steep used in the method according to the invention can, in particular, be the one described in patent U.S. Pat. No. 4,359,528 or again those described in patent applications EP 724 841 and EP 819 702 of which the Assignee is the owner.

As regards atomisation of the corn-steep enriched with metal salt, any type of material known to the skilled person can be used.

The inventors have demonstrated that pulverulent corn-steep according to the invention could be manufactured advantageously using, for instance, an atomisation tower of the NIRO type.

Advantageously, one can choose an air intake temperature of between 150 and 250° C. and flows of incoming materials such that the temperature of the air leaving the tower will be between 80 and 150° C.

The pulverulent corn-steep obtained according to the method of the invention can be afterwards made into tablets, for instance, in alternating presses in the presence of a lubricant.

The pulverulent corn-steep according to the invention can be used with advantage as a nutrient substance in the preparation of culture media for the fermentation industry. It can also be used in the fields of food industry or alimentation, animal nutrition or other fields.

Unlike the pulverulent corn-steeps of prior art, the corn-steep according to the invention retains its initial biochemical characteristics. Furthermore, it possesses the advantageous characteristic of being compressible which is of particular interest in industrial practice because of the risks and disadvantages linked to handling powders. Moreover, the tablet form permits meticulous dosage in the preparation of culture media.

The invention will be understood even better with the aid of the following examples which are not restrictive and which account for only certain embodiments and for certain advantageous properties of the pulverulent corn-steep according to the invention.

EXAMPLE I

Preparation of Pulverulent Corn-steep According to the Invention

A liquid corn-steep is prepared with 50% dry matter, implementing the method described in patent EP-A-0 819 702 in the name of the Assignee. To this is added 3.2% by weight (dry/dry) of MgO in the form of a 100 g/l suspension in a tank with a thermostat at 50° C., whilst stirred.

The pH of the liquid corn-steep enriched with MgO is 5.7.

Then, atomisation is carried out in a NIRO tower under the following conditions:

input temperature : 200° C.

output temperature :96° C.

speed of turbine: 15,000 rotations per minute evaporation capacity: 80 litres per hour The lactic acid content of the corn-steep obtained is 14% by weight.

The particles do not stick to the walls of the atomising chamber.

The powder is dense and falls down quickly from the cyclone.

EXAMPLE 2

Application of the Pulverulent Corn-steep According to the Invention to the Growth of Organisms The study described below consists in following the increase in the number of cells according to time in a culture medium containing a given concentration of the pulverulent corn-steep according to the invention. This is done in comparison with culture media containing the same equivalence in nitrogen brought by other sources.

The study relates to the growth of a strain of *Saccharomyces cerevisiae*. The analysis of the culture worts is carried out at 0, 24 and 48 hours of incubation by determining cellular mortality by flux cytometry (CHEMFLOW CHEMUNEX).

A preculture medium is prepared by adding to demineralised water 50 g/l glucose, 5 g/l liquid corn-steep with 50% dry matter, 5 g/l peptone. 3 g/l $KHPO_4$ and 1 g/l $MgSO_4$, $7H_2O$. The medium is sterilised for 20 minutes at 120° C. after adjustment of the pH to 5.7. 50 ml of medium are then seeded by a loop of cells coming from a nutrient medium treated with gelose CGA (MERCK).

The preculture is incubated for 24 hours at 30° C. whilst being stirred at 250 rotations per minute.

A culture medium is prepared by adding to demineralised water 100 g/l glucose and 5 g/l pulverulent corn-steep according to the invention.

By way of comparison, culture media are prepared with 10 g/l liquid corn-steep with 50% dry matter, 10 g/l hydrolysed not atomised liquid corn-steep (with 50% dry matter) as described in patent EP-A-819 702 in the name of the Assignee, or 3 g/l yeast extract (YEAST EXTRACT marketed by the company DIFCO). The volume of the medium is 50 ml in Erlenmeyer flasks of 500 ml with 4 baffles at the bottom. These media are sterilised for 20 minutes at 120° C.

Each of these media is seeded with 5 ml of the same preculture of *S. cerevisae*. The incubation is carried out at 30° C. whilst stirring at 250 rpm for 48 hours.

The analysis by flux cytometry is made according to the protocol laid down by the company CHEMUNEX for the use with of the apparatus Chem Flow Auto System 3.

Results

The results are expressed as a percentage of dead cells present in the total population (estimated at $10^{-8}$ cfu/g).

|  | 0 h | 24 h | 48 h |
|---|---|---|---|
| LCS(*) | 41.8% | 11.4% | 12.9% |
| Hydrolysed not atomised LCS | 41.8% | 10.5% | 11.4% |
| CS of the invention | 41.8% | 11.2% | 11.8% |
| Yeast extract | 41.8% | 46.2% | 56.4% |

(*)liquid corn-steep.

The results show better preservation of cellular viability for cells cultivated on atomised pulverulent corn-steep according to the invention compared with cells cultivated on yeast extract.

These same results show, for cells cultivated on corn-steep according to the invention, preservation of cellular viability similar to that obtained for cells cultivated on liquid corn-steep, hydrolysed or not.

Atomising has therefore not altered in any way the nutrient qualities of the corn-steep. Moreover, the significant density of the powder permits easier handling than the yeast extract, in particular when weighing.

What is claimed is:

1. A method of preparing a pulverulent corn-steep containing no drying substrate, said corn-steep containing lactic acid and having a lactic acid content greater than or equal to 10% by weight of dry matter, the method comprising the following steps:

a) enrichment of the liquid corn-steep by at least one metal salt, b) atomization of the enriched liquid corn-steep, c) recovery of the pulverulent corn-steep thus obtained.

2. The method according to claim 1, wherein the metal salt is selected from the group consisting of zinc, magnesium, calcium, strontium, barium, lithium salts, on their own or mixed with one another.

3. The method according to claim 2, wherein the metal salt is magnesium oxide.

* * * * *